(12) United States Patent
Wei et al.

(10) Patent No.: US 9,420,947 B2
(45) Date of Patent: Aug. 23, 2016

(54) AUTOMATIC ALIGNMENT OF AN IMAGER

(71) Applicant: Optovue, Inc., Fremont, CA (US)

(72) Inventors: Jay Wei, Fremont, CA (US); Jing Cui, Fremont, CA (US); Tao Huang, Fremont, CA (US); Dragos Stanescu, San Jose, CA (US)

(73) Assignee: OPTOVUE, INC., Fremont, CA (US)

( * ) Notice: Subject to any disclaimer, the term of this patent is extended or adjusted under 35 U.S.C. 154(b) by 261 days.

(21) Appl. No.: 14/191,973

(22) Filed: Feb. 27, 2014

(65) Prior Publication Data
US 2014/0240674 A1 Aug. 28, 2014

Related U.S. Application Data

(60) Provisional application No. 61/770,289, filed on Feb. 27, 2013.

(51) Int. Cl.
*A61B 3/14* (2006.01)
*A61B 3/10* (2006.01)
*A61B 3/15* (2006.01)

(52) U.S. Cl.
CPC ........... *A61B 3/102* (2013.01); *A61B 3/152* (2013.01)

(58) Field of Classification Search
USPC ................................................ 351/200–246
See application file for complete search history.

(56) References Cited

U.S. PATENT DOCUMENTS

| | | | |
|---|---|---|---|
| 2005/0110951 A1 | 5/2005 | Yancey et al. | |
| 2008/0278687 A1 | 11/2008 | Somani | |
| 2009/0027685 A1* | 1/2009 | Abe | A61B 3/102 356/477 |
| 2009/0046248 A1 | 2/2009 | Niven | |
| 2009/0153797 A1* | 6/2009 | Allon | A61B 3/12 351/206 |
| 2011/0176110 A1* | 7/2011 | Bublizt | A61B 3/113 351/206 |
| 2012/0249961 A1 | 10/2012 | Muto | |

OTHER PUBLICATIONS

PCT International Search Report and the Written Opinion mailed Jun. 6, 2014, in related International Application No. PCT/US2014/019062.

* cited by examiner

*Primary Examiner* — Mohammed Hasan
(74) *Attorney, Agent, or Firm* — Haynes and Boone, LLP

(57) ABSTRACT

Embodiments of automatically aligning imager are presented. In accordance with some embodiments, an imaging system includes an adjustment stage; an auto-alignment optics mounted on the adjustment stage and coupled to image an object, the auto-alignment optics including at least one video camera providing an image of the object; imaging scanning optics mounted on the adjustment stage and coupled to scan the object; an imager coupled to the imaging scanning optics; and a processor coupled to the adjustment stage and the auto-alignment optics, the processor executing instructions to receive the image of the object and adjust the adjustment stage to align the optics with the imaging scanning optics.

19 Claims, 6 Drawing Sheets

AUTOMATIC ALIGNMENT OF AN IMAGER

RELATED APPLICATIONS

The present application claims priority to U.S. Provisional Application No. 61/770,289, filed on Feb. 27, 2013, which is herein incorporated by reference in its entirety.

BACKGROUND

1. Technical Field

Embodiments of the present invention are related to imaging and, in particular, to an imager that operates automatically or semi-automatically to generate an image.

2. Discussion of Related Art

Imaging technologies continue to play a large role in various evaluation techniques. Optical Coherence Tomography (OCT), for example, has evolved from an ophthalmic imaging device, which was adopted by a majority of retina specialists and major institutes over 10 years ago, to a daily clinical tool used in many ophthalmologist and optometrist offices. A majority of patients come to the office with some symptom of eye conditions that can be examined by the OCT imager. The volume of patients examined by an OCT technique has skyrocketed in recent years. On the other hand, it is common for operators in a small clinical office environment to have less experience and skill in using advanced ophthalmic imaging systems. Often the inexperience of the operators results in less effective OCT imagery and lengthy examination times, which limits the use of such instruments.

Traditional OCT design requires operators to be skillful in using a joystick for aligning the scanner optics to the patient's eye and optimizing the OCT signal strength and position before capturing an image. It often requires multiple steps to align the system and optimize the OCT signal. Such alignment and optimization requires the operator to perform multiple alignment and optimization steps in a very short time, especially before the patient is fatigued by the examination. This process often requires extensive training and relies on the experience of the operator to acquire the necessary skills.

Therefore, there is a need to develop imagers such as OCT imagers that are easy to use and require short examination times.

SUMMARY

In accordance with aspects of the present invention, an imager that provides an automatic alignment is provided. An imaging system according to some embodiments includes an adjustment stage; an auto-alignment optics mounted on the adjustment stage and coupled to image an object, the auto-alignment optics including at least one video camera providing an image of the object; imaging scanning optics mounted on the adjustment stage and coupled to scan the object; an imager coupled to the imaging scanning optics; and a processor coupled to the adjustment stage and the auto-alignment optics, the processor executing instructions to receive the image of the object and adjust the adjustment stage to align the optics with the imaging scanning optics.

A method of aligning an imaging system according to some embodiments of the present invention includes receiving a far camera image of an object from a far camera into a processor, the far camera coupled through non-telecentric optics to the object; centering the object by adjusting a stage on which the far camera and non-telecentric optics are mounted relative to the object based on a feature detected in the far camera image by the processor; and the processor moving the stage closer to the object until the object has reached a predetermined size in the far camera image.

These and other embodiments are further discussed below with respect to the following figures.

The drawings are not to scale and no meaning is to be inferred from relative sizes of components. Components with the same identifiers have the same or similar function.

DETAILED DESCRIPTION

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

This description and the accompanying drawings that illustrate inventive aspects and embodiments should not be taken as limiting—the claims define the protected invention. Various changes may be made without departing from the spirit and scope of this description and the claims. In some instances, well-known structures and techniques have not been shown or described in detail in order not to obscure the invention.

The embodiments described below are provided in order to demonstrate and further illustrate certain aspects of the present invention and are not to be construed as limiting the scope thereof. As a particular example, the object under investigation below is an eye. This has to be understood as merely a way to help the description and not as a restriction of the application of the present invention. As such, where the term "eye" is used, a more general transparent and scattering object or organ may be sought instead. Further, specific embodiments have been described relative to an OCT system. However, it should be understood that other imaging system may be used as well and that discussion of an OCT system is for convenience only. Although various embodiments that incorporate the teachings illustrated and described in detail herein, a person of ordinary skill in the art can readily devise other various embodiments that incorporate the teachings of this subject invention.

In accordance with aspects of embodiments of the present invention, manual operation of an imager is replaced by automatic alignment scanner optics to the patient's eye, automatic optimizing of the imager signal strength and position, and automatic capturing and storing of images can be performed. Consequently, an automatic patient eye alignment system and method that can be employed on a non-invasive optical imaging and measurement device, such as an OCT imager, is disclosed. Although throughout the description below, an OCT imager is described, the invention should not be limited to OCT imagers and can be utilized with other non-invasive optical imaging systems.

Figure 1A:
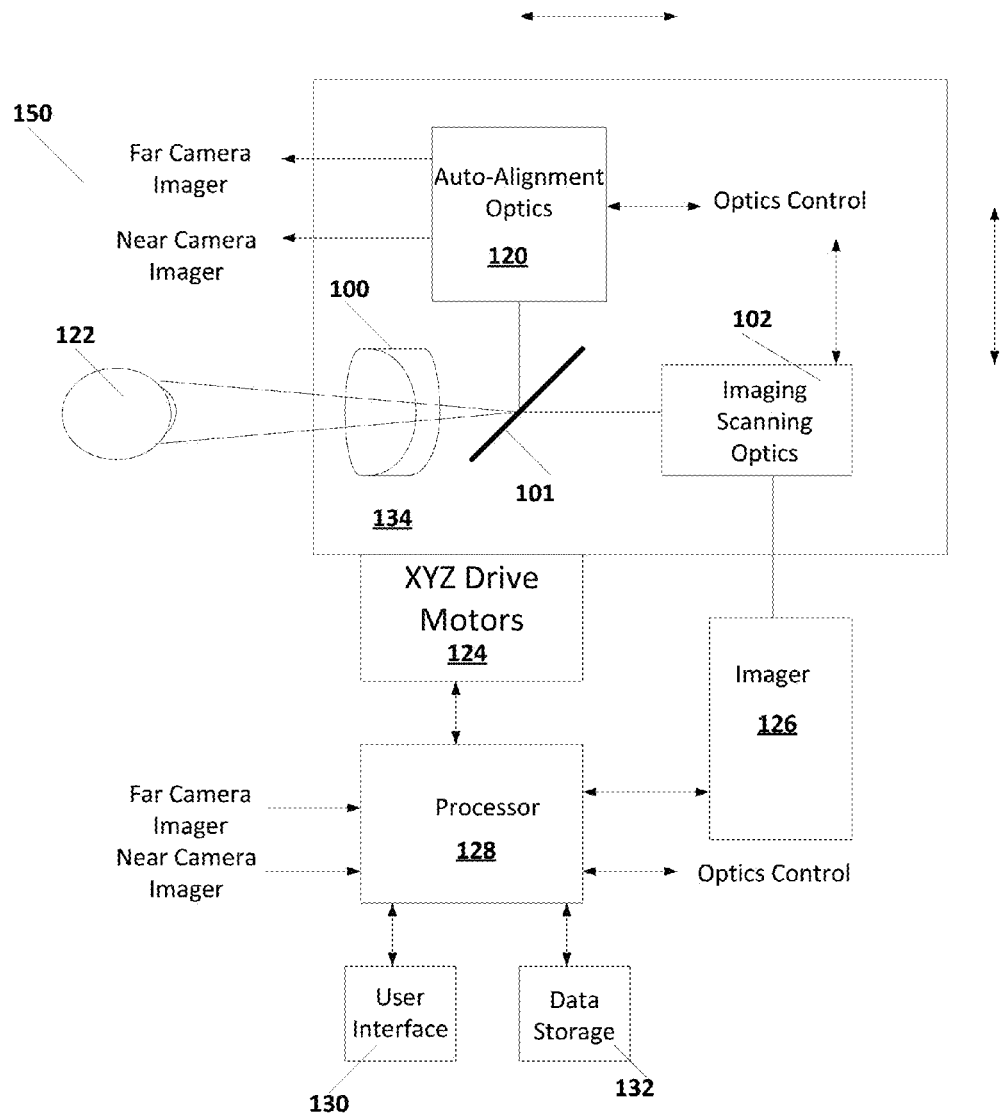
FIG. 1A illustrates an automatic alignment imager according to some embodiments of the present invention.

FIG. 1A illustrates an auto-alignment imager system 150 according to some embodiments of the present invention. As shown in FIG. 1A, light from an imaging scanning optics 102 and an auto-alignment optics 120 are combined in a beam splitter 101 and directed toward a patient's eye 122 through lens system 100. As shown in FIG. 1A, scanning optics 102, alignment optics 120, beam splitter 101, and lens system 100 are mounted on an XYZ translations stage 134 that is driven by XYZ drive motors 124. XYZ drive motors 124 are driven by a processor 128, which controls the positioning of XYZ stage 134. Processor 128 can be any processor system and typically includes one or more microprocessors along with associated volatile and non-volatile memory and data storage drives. Processor 128 can also be coupled to a user interface 130, which provides video output and operator input, and data storage 132, which can include removable media for storage of images and other data.

As shown in FIG. 1A, processor 128 receives images of the eye from a far camera and a near camera in alignment optics 120 and processes the images to position XYZ stage 134 relative to eye 122. Further, processor 128 receives data from imager 126 in order to optimize the image from imager 126. Once alignment is complete, imager 126 can take an image, which processor 128 can display on user interface 130 and store the image on data storage 132. In some embodiments, once alignment is complete, processor 128 can disengage alignment optics 120 to not interfere with the imaging processes from imager 128 and scanning optics 102.

Figure 1B:
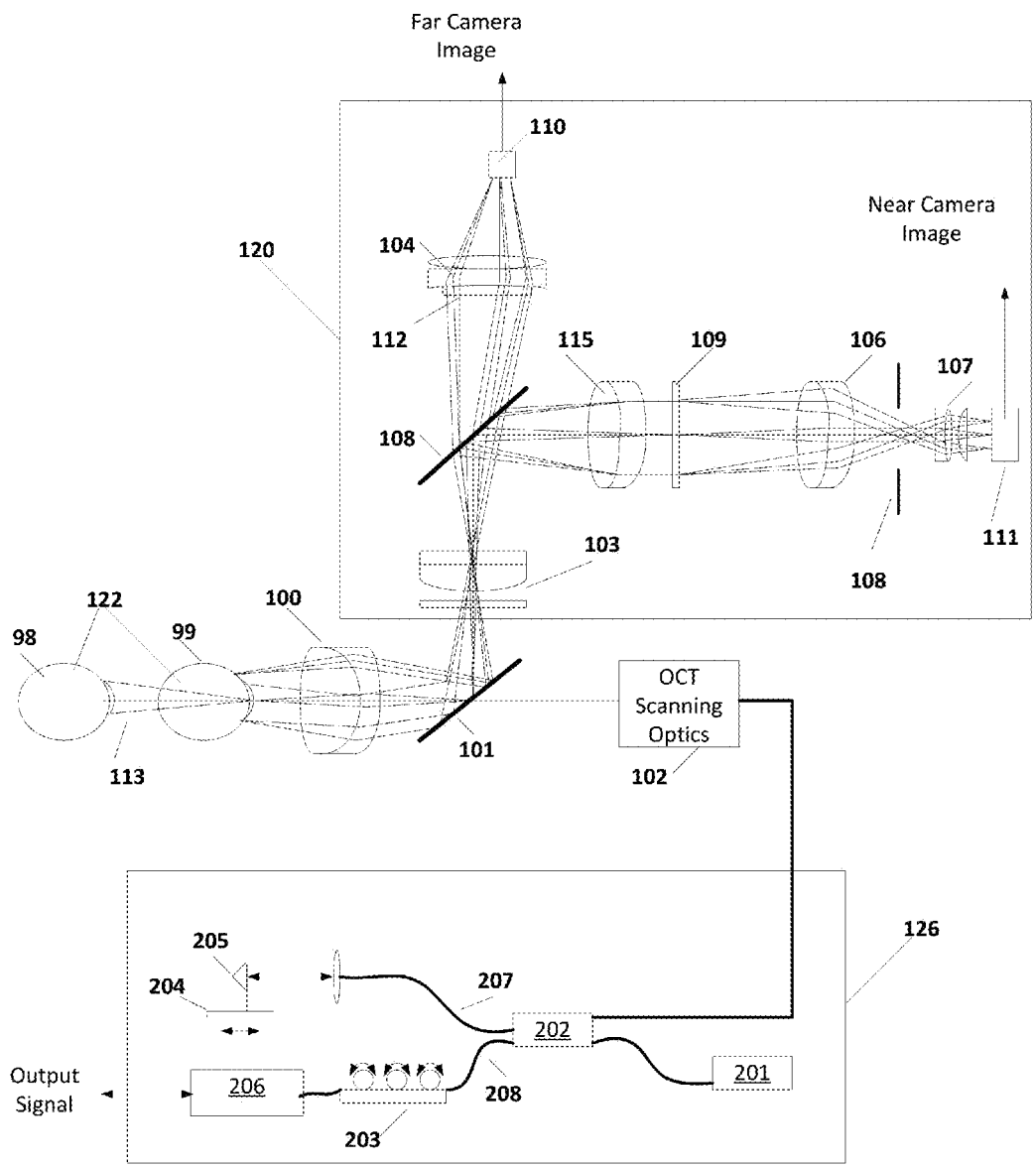
FIG. 1B is a schematic of the automatic alignment optics with an OCT imager in accordance with some embodiments of the present invention.

FIG. 1B illustrates alignment optics 128 and an example of imager 126. As shown in FIG. 1B, imager 126 is an OCT imager, but as discussed above other imagers can be used. As is further shown in FIG. 1B, beam splitter 101 combines light provided by OCT scanning optics 102 and light provided by auto-alignment optics 120 and directs the combination through optics 100 to eye 122.

In the example shown in FIG. 1B, imager 126 is an OCT interferometer that includes a light source 201, a coupler 202, a spectrometer and detector 206, and a reference mirror 205 mounted on a motorized stage 204. As shown in FIG. 1B, a polarization controller 203 mounted within detector arm 208 can include one or more polarization wheels that are driven by individual motors.

As shown in FIG. 1B, alignment optics 120 includes two imaging paths separated at beam splitter 108. A far path ending in far camera 110 images eye 120 in a far position 98. A near path ends in near camera 111, which images eye 122 if it is in a near position 99. In some embodiments, LEDs can be provided in the scan head between lens 100 and near position 99 and are positioned to provide a light pattern on eye 122 which is reflected back to cameras 110 and 111 The first step in aligning eye 122 to the scanner optics is to locate far camera 110 to the eye 122. Processor 128 can, then, turn on far camera 110 and receive the far camera image from far camera 110. The initial field-of-view of far camera 110 should be large enough to allow eye 122 to be easily viewed by camera 110. The optics design for imaging in far camera 110 can be a non-telecentric optical system with low numerical aperture.

FIG. 1B illustrates an example of a non-telecentric optical system with a low numerical aperture between eye 122 and far camera 110. The eye 122 at position 98 is at a far distance location. Eye 122 can be imaged through lens system 100, reflected by beamsplitter 101, through lens group 103, through beamsplitter 108, and through a lens group 104 to the sensors of far camera 110. Because of the low numerical aperture, controlled by aperture 112, the optics provides a long depth of focus for far camera 110 to view eye 122. The eye image is close to focus even when the distance between eye 122 and scanner optics, starting at lens system 100, varies over a large range of distances. However, because it is a non-telecentric system, as shown in FIG. 1B, the ray fan 113 is not parallel to each other and the field of view changes with the changing of the distance between eye 122 and lens system 100 or scanning optics 102.

Figures 2A, 2B, 2C:
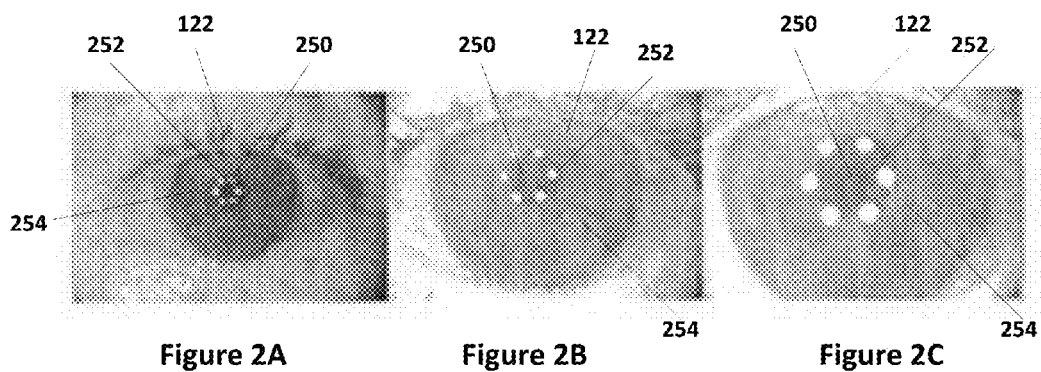
FIGS. 2A-2C show eye images as detected by the far camera illustrated in FIG. 1.

FIGS. 2A, 2B, and 2C show images of eye 122 at three distances from far camera 110. FIG. 2A is an image from far camera 110 with eye 122 at a far distance. FIG. 2B is an image from far camera 110 when eye 122 is at a close distance. FIG. 2C is an image from far camera 110 when eye 122 is at the desired working distance. All three images are in focus, so the image algorithm operating on processor 128 can easily detect the size of the features on the eye, for example pupil 250 or iris 254 of eye 122. Further, the reflection of the illumination LEDs (six bright dots 252 in this example) are visible in the images. From the size and location of these features, distance information can be acquired. Also, because the image of eye 122 is in focus, the center of the eye pupil 152 can be determined by image processing algorithms operating on processor 128. With the distance and the centering information, processor 128 can guide XYZ stage 134 to move scanner optics (e.g., lens system 100) closer to eye 122. In some embodiments, processor 128 moves XYZ stage 134 until the size of eye 122 in the image captured by far camera 110 is a specific predetermined size, or in some cases until the image is too large and the features on the eye are outside of the field of view of far camera 110. At that point, processor 128 can move XYZ stage 134 to achieve a rough alignment using the image detected by far camera 110.

In some embodiments, once the rough alignment has been accomplished using far camera 110, far camera 110 is shut off and near camera 111 is activated to continue fine tuning the scanner optics position. In some embodiments, the optics for near camera 111 is a telecentric optical system with larger numerical aperture. At this point, eye 122 is at location 99, located near the desired working distance position. Eye 122 is imaged through lens 100, reflected by beamsplitter 101, through lens group 103, reflected by a beam splitter 108, and passed through lens group 105 to form an intermediate image 109. Intermediate image 109 is then relayed by lens group 106 and lens group 107 to the sensors of near camera 111. Because of the large numerical aperture, controlled by an aperture 108, the depth of focus is very short at near camera 111. In other words, the image of eye 122 at near camera 111 will be in focus only when eye 122 is in the desired working distance from the scanner optics starting at lens system 100. Also, because the optics through which the image passes through to reach near camera 111 is substantially telecentric, the magnification is constant and the eye image size will not substantially vary when eye 122 is not in the desired position. This unique feature allows an imaging algorithm operating on processor 128 to determine distance of eye 122 from the scanner optics using the focus of the image. As a result, processor 128 can use the positioning of XYZ stage 134 to focus the image from near camera 111.

Figures 3A, 3B:
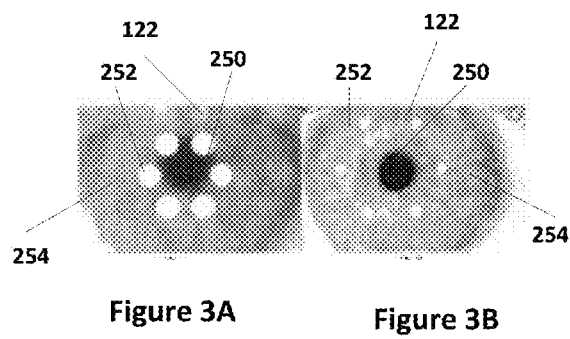
FIGS. 3A and 3B show eye images as detected by the near camera illustrated in FIG. 1.

FIGS. 3A and 3B show images of eye 122 from near camera 111 and the effect of the eye image relative to the distance of eye 122 from the near eye camera 111. FIG. 3A shows the eye 122 not being at the desired working distance, but is at the same distance as shown in FIG. 2B. FIG. 3B shows the patient's eye in the desired working distance. Near camera 111 is very sensitive to the distance to eye 122 with larger numerical aperture, so it can be used to fine tune the patient's working distance with high accuracy.

Therefore, in accordance with some embodiments, by using the image from far camera 110 the scanner optics is moved relative to eye 122 from far distance as illustrated in FIG. 2A to the near distance as illustrated in FIG. 2C. Then, far camera 110 is turned off and near camera 111 is activated to acquire the image shown in FIG. 3A. The scanning optics is then moved to the desired working distance and fine-tuned to arrive at the focused image as shown in FIG. 3B. These steps automatically align the patient's eye to the position ready for an image scan such as an OCT scan.

To acquire an OCT image, the optical path length of reference arm 207 to a reference mirror 205 of the interferometer needs be adjusted until it matches the optical path length of the sample arm 208 to eye 122. This can be realized by motorizing reference mirror mount 204, which can be driven by processor 128 in some embodiments. At this point, imager 126 and scanning optics 102 are activated and processor 128 drives motorized mirror mount 204 until an OCT image is received in detector 206.

Figure 1C:
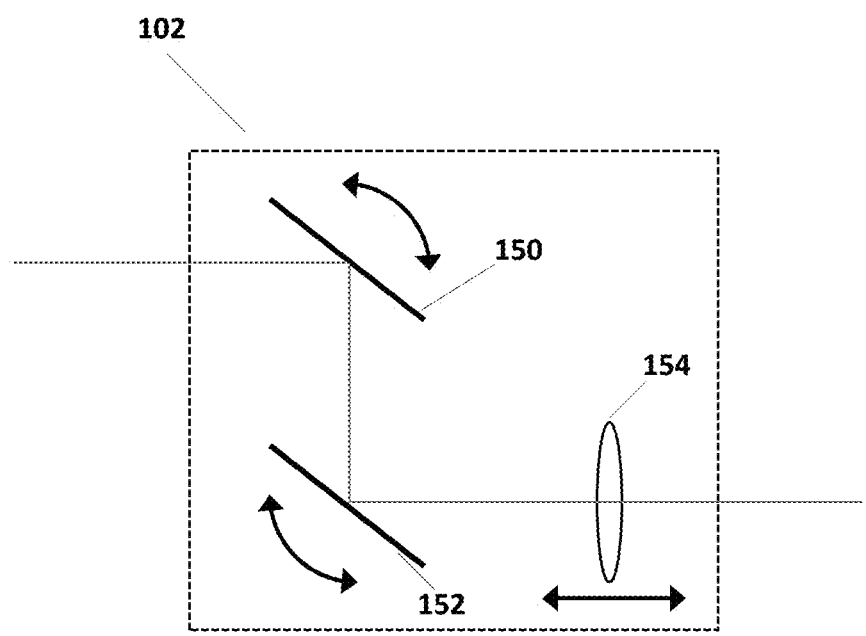
FIG. 1C is a schematic of the imaging scanning optics illustrated in FIGS. 1A and 1B.

After the OCT image is acquired, the next step is to optimize the OCT signal strength. This is partially accomplished by adjusting scanning optics 102. FIG. 1C illustrates an embodiment of scanning optics 102. As shown in FIG. 1C, scanning optics 102 includes scanning mirrors 150 and 152 and an adjustable fiber collimator lens 154. Scanning mirrors 150 and 152 scan the beam in a defined pattern across eye 122. By adjusting a fiber collimator lens 154 to focus the OCT beam onto eye 122, processor 128 can maximize the OCT signal. The position of collimator lens 154 that maximizes the OCT signal can be determined by examining the overall OCT signal strength and adjusting the fiber collimator lens 154 to maximize the OCT signal strength.

After optimizing the focus using collimator lens 154, the OCT signal can be further maximized by optimizing the polarization of the OCT beam. This can be achieved by rotating the polarization controller 203 until the signal strength is maximized. Polarization controller 203 is shown in sample arm 208 in FIG. 1B, however it may also be in reference arm 207. Finally, the OCT image might be tilted onto one side, caused by the scan beam optical path length in eye 122 being unequal from one side of eye 122 to the other side of eye 122. This can be adjusted by moving the scan beam position on the pupil plane transversely until the OCT image is leveled. Processor 128 can adjust the positions of steering mirrors 150 and 152 in order to adjust the tilt of the resulting image.

Figure 4A:
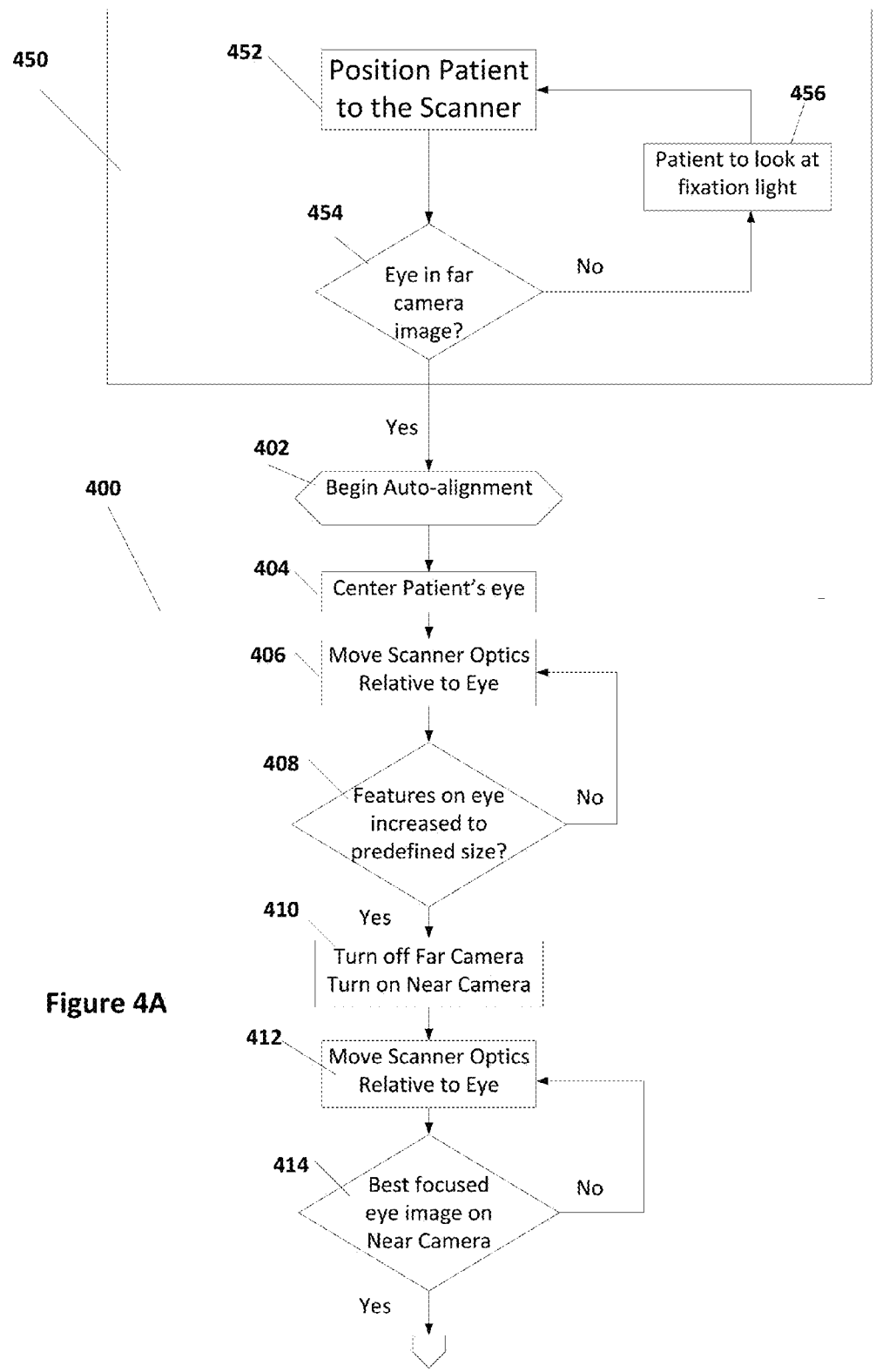
FIGS. 4A and 4B illustrate a flow diagram of an automatic alignment imaging system according to some embodiments of the present invention.
Figure 4B:
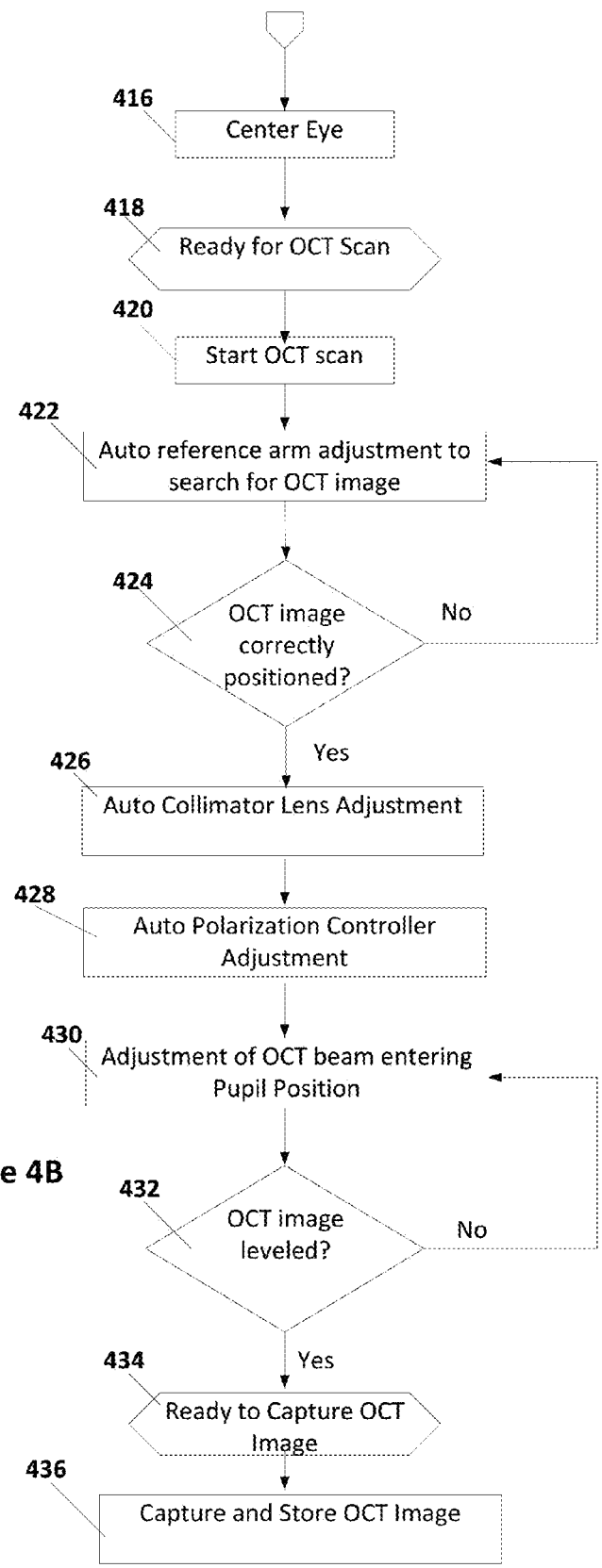

FIGS. 4A and 4B illustrate an algorithm 400 that can be executed by processor 128 to implement auto alignment according to some embodiments of the present invention. As shown in FIG. 4A, before algorithm 400 can be started a procedure 450 is performed, usually under the direction of an operator of the imaging system 150. Procedure 450 starts in step 452 with positioning the patent relative to imaging system 150 and, in particular, to positioning eye 122 roughly relative to imaging system 150. In step 454, the operator checks to make sure that eye 122 is visible to far camera 110. If not, then the patient is directed to look at a fixation light in step 456 and is repositioned in step 452. If eye 122 is visible to far camera 110, then algorithm 400 can be implemented. After algorithm 400 is implemented, further adjustments are made automatically at the direction of processor 128 executing instructions that implement algorithm 400.

In step 402, auto-alignment algorithm 400 begins. In some embodiments, algorithm 400 can be initiated by the operator of system 150 after the patient has been positioned relative to system 150.

In step 404, using the image of eye 122 from far camera 110, processor 128 centers eye 122 by moving XYZ stage 134 to align, for example, pupil 250 to the optical axis of system 150. Once eye 122 is centered, algorithm 400 moves to step 406. In step 406, processor 128 moves XYZ stage 134 so that lens system 100 is closer to eye 122. This motion is accomplished incrementally so that after an initial incremental step, algorithm 400 proceeds to step 408 to check whether the eye 122 is positioned appropriately close to lens system 100. In step 408, if the features of eye 122 are increased to a predefined size, then algorithm 400 proceeds to step 410, otherwise algorithm 400 returns to step 406 where processor 128 again moves XYZ stage 134 closer to eye 122.

In step 410, far camera 110 is shut off and near camera 111 is activated. At this step, a fine alignment is begun using images from near camera 111. In step 412, processor 128 moves XYZ stage 134 relative to eye 122. In step 414, processor 128 determines whether the image received from near camera 111 is the best focus available. If not, then algorithm 400 returns to step 412 to move XYZ stage 134 relative to eye 122 in a direction of increased focus.

If the focus of the image from near camera 111 is achieved, then algorithm 134 proceeds to step 416. In step 416, the image from near camera 111 is analyzed by processor 128 to locate features of eye 122 and the features are used to move XYZ stage 134 so that eye 122 is centered.

After step 416, imager system 150 is optically aligned with eye 122. Near field 111 can be shut off and, as shown in step 418, imager system 150 is ready to begin imaging. In the example provided here, as discussed above, the imager is an OCT imager and therefore imager system 150 is an OCT system. However, other imaging systems can be used.

In step 420, OCT imager 126 is started and scanning optics 102 is activated. As shown in FIGS. 1A and 1B, processor 128 receives OCT data from spectrometer and detector 206. While monitoring the signal from spectrometer and detector 206, processor 128 can adjust the location of reference mirror 205 by adjusting motorized mount 204 until an OCT image is achieved. As shown in FIG. 4B, in step 422 the location of reference mirror 205 is adjusted and in step 424 processor 128 determines whether an OCT image is achieved and correctly positioned. Once the OCT image is achieved, algorithm 400 proceeds to step 426.

In step 426, processor 128 adjusts the collimater and lens to maximize the OCT signal. Once that adjustment is completed, algorithm 400 proceeds to step 428 where polarizer 203 is adjusted to maximize the OCT signal. Once the polarizer is adjusted, algorithm 400 proceeds to steps 430 and 432. In step 430, the OCT beam is adjusted and in step 432 processor 128 checks to be sure that the OCT image produced is leveled.

Once the adjustments to OCT imager 126 are complete, the algorithm 400 is ready to capture an OCT image as indicated in step 434. Consequently, in step 436 an OCT image is captured and stored.

As is shown in FIGS. 4A and 4B, once the operator has positioned the patient in front of imaging system 150, imaging system 150 automatically aligns itself to eye 122, adjusts imager 126, and captures an image without further input from the operator. Positioning the patient can be as simple as seating the patient in front of imaging system 150 with head against a mount and eye positioned against an eyepiece.

The above detailed description is provided to illustrate specific embodiments of the present invention and is not intended to be limiting. Numerous variations and modifications within the scope of the present invention are possible. The present invention is set forth in the following claims.

What is claimed is:

1. An imaging system, comprising:
an adjustment stage;
an auto-alignment optics mounted on the adjustment stage and coupled to image an object, the auto-alignment optics including a far camera and a near camera;
imaging scanning optics mounted on the adjustment stage and coupled to scan the object;
an imager coupled to the imaging scanning optics; and
a processor coupled to the adjustment stage and the auto-alignment optics, the processor executing instructions to:
receive a far-camera image from the far camera;
adjust the adjustment stage to center the object based on the far-camera image;
adjust the adjustment stage to position an object distance based on the far-camera image;
receive a near-camera image from the near camera;
adjust the adjustment stage to focus the near-camera image;
adjust the adjustment stage to center the object based on the near-camera image; and
align the auto-alignment optics with the imaging scanning optics.

2. The imaging system of claim 1, wherein the auto-alignment optics include a non-telecentric optical path between the far camera and the object and a telecentric optical path between the near camera and the object.

3. The imaging system of claim 2, wherein the near camera includes a large numerical aperture and the far camera includes a low numerical aperture.

4. The imaging system of claim 1, wherein the processor executes further instructions to:
adjust the imager relative to the object; and
capture an image from the imager.

5. The imaging system of claim 4, wherein the imager is an OCT imager and instructions to adjust the imager include adjusting a position of a reference mirror in a reference arm to obtain an OCT image.

6. The imaging system of claim 5, wherein instructions to adjust the imager further include adjusting polarization to maximize an OCT signal.

7. The imaging system of claim 5, wherein instructions to adjust the imager further include adjusting a tilt of the OCT image relative to the object.

8. The imaging system of claim 5, wherein the image scanning optics include fiber collimator lens and wherein the processor further executes instructions to adjust the fiber collimator lens to focus an OCT signal.

9. The imaging system of claim 1, wherein adjusting the adjustment stage to center the object includes determining a feature of the object and adjusting the adjustment stage to position the feature.

10. The imaging system of claim 9, wherein the feature is a pupil of an eye.

11. A method of aligning an imaging system, comprising:
receiving, by a processor, a far-camera image of an object from a far camera, the far camera coupled through a first set of optics to the object;
centering the object by adjusting a stage on which the far camera and the first set of optics are mounted relative to the object based on a feature detected in the far-camera image by the processor;
adjusting the stage to position an object distance based on the far-camera image;
receiving, by the processor, a near-camera image of the object from a near camera, the near camera coupled through a second set of optics to the object;
adjusting the stage to focus the near-camera image; and
adjusting the stage to center the object based on the near-camera image.

12. The method of claim 11, wherein the first set of optics are non-telecentric and the second set of optics are telecentric.

13. The method of claim 11, wherein adjusting the stage to position an object distance based on the far-camera image includes moving the stage closer to the object until the object has reached a predetermined size in the far-camera image.

14. The method of claim 13, further comprising:
adjusting an imager relative to the object, the imager coupled to imaging scanning optics, the image scanning optics mounted on the stage and coupled to scan the object; and
capturing an image from the imager.

15. The method of claim 14, wherein the imager is an OCT imager and adjusting the imager includes adjusting a position of a reference mirror in a reference arm to obtain an OCT image.

16. The method of claim 15, wherein adjusting the imager includes adjusting polarization to maximize an OCT signal.

17. The method of claim 15, wherein adjusting the imager includes adjusting a tilt of the OCT image relative to the object.

18. The method of claim 14, centering the object by adjusting a stage includes determining a feature of the object and adjusting the stage to position the feature.

19. The method of claim 18, wherein the feature is a pupil of an eye.

* * * * *